(12) United States Patent
Scimone et al.

(10) Patent No.: US 10,654,165 B2
(45) Date of Patent: May 19, 2020

(54) CUTTING DEVICE

(71) Applicant: Slice, Inc., San Jose, CA (US)

(72) Inventors: Thomas Scimone, Campbell, CA (US);
Scot Herbst, Santa Cruz, CA (US);
William W Hunter, Santa Cruz, CA (US); Robert Joseph Gallegos, Fremont, CA (US)

(73) Assignee: Slice, Inc., San Jose, CA (US)

( * ) Notice: Subject to any disclaimer, the term of this patent is extended or adjusted under 35 U.S.C. 154(b) by 66 days.

(21) Appl. No.: 15/943,854

(22) Filed: Apr. 3, 2018

(65) Prior Publication Data

US 2018/0290286 A1 Oct. 11, 2018

Related U.S. Application Data

(60) Provisional application No. 62/482,562, filed on Apr. 6, 2017.

(51) Int. Cl.
| | |
|---|---|
| *B25G 3/28* | (2006.01) |
| *A61B 17/3211* | (2006.01) |
| *B25G 3/10* | (2006.01) |
| *B26B 3/00* | (2006.01) |
| *B26B 29/02* | (2006.01) |
| *A61B 17/00* | (2006.01) |

(52) U.S. Cl.
CPC ............ *B25G 3/28* (2013.01); *A61B 17/3211* (2013.01); *B25G 3/10* (2013.01); *A61B 2017/00477* (2013.01); *A61B 2017/00526* (2013.01); *B26B 3/00* (2013.01); *B26B 29/025* (2013.01)

(58) Field of Classification Search
CPC ...... A61B 17/3213; A61B 2017/32113; A61B 17/3211; A61B 2017/00477; A61B 2017/00526; B25G 3/10; B25G 3/28
See application file for complete search history.

(56) References Cited

U.S. PATENT DOCUMENTS

| | | | | |
|---|---|---|---|---|
| 1,636,062 | A * | 7/1927 | MacLure | ........... A61B 17/3213 30/333 |
| 5,417,518 | A * | 5/1995 | Bierwith | ................... B25G 3/28 37/457 |
| 5,896,621 | A * | 4/1999 | Lindgren | ................. B25G 3/10 16/114.1 |
| 8,413,339 | B2 * | 4/2013 | Ranieri | ................... B26B 5/002 30/162 |
| 2004/0111895 | A1 * | 6/2004 | Huang | .................... B26B 5/002 30/162 |

* cited by examiner

*Primary Examiner* — Omar Flores Sanchez
(74) *Attorney, Agent, or Firm* — Ellenoff Grossman & Schole LLP; James M. Smedley; Alex Korona

(57) ABSTRACT

A cutting device is disclosed. The cutting device has a body member having a cavity that extends from an opening at a front end portion of the body member toward a back end portion of the body member. The cutting member also has a cutting member partially disposed in a first portion of the cavity, and an insert member disposed in a second portion of the cavity. The cavity narrows in a direction extending from the front end portion toward the back end portion. A width of the first portion of the cavity is greater than a width of the second portion of the cavity.

19 Claims, 2 Drawing Sheets

CUTTING DEVICE

RELATED APPLICATIONS

This application claims the benefit of U.S. Provisional Patent Application Ser. No. 62/482,562 filed Apr. 6, 2017, which is hereby incorporated by reference in its entirety.

TECHNICAL FIELD

The present invention generally relates to cutting devices. For example, at least some exemplary embodiments of the present disclosure relate to disposable scalpels having a blade holding cavity that comprises a side chamber with an insert that together with the walls of the cavity secures the blade.

BACKGROUND

A scalpel is a small and sharp bladed instrument commonly used for surgery, anatomical dissection, and various arts and crafts (e.g. craft knife or hobby knife). Scalpels typically have two parts, a cylindrical body (often flat), and a short blade, held in a cavity in the body. Scalpels may be re-usable or disposable. Re-usable scalpels have removable blades, to replace the blade after single surgical use, or when the blade becomes dull. A disposable scalpel is configured with a permanent blade, often for single use, after which the entire instrument may be discarded. Disposable scalpels are not configured for the blade to be removed and exchanged. Disposable scalpels are often used in greater numbers as they are disposed of immediately after use, and are often mass produced accordingly. In production, and especially mass production, tolerances for measurements including dimensions of the blade holding cavity and the blade, for example the blade's height or width, can be an issue that affects the secure fit of the blade. Depending on tolerances for blade width and corresponding holding cavity, a traditional friction fit between blade holding cavity and blade may not adequately hold the blade, and may allow unacceptable blade movement. This can create potentially hazardous situations if the precision of the cut is compromised, or worse, if the blade falls out of the holding cavity entirely.

Therefore, there is a need in the art for a disposable scalpel that better secures the blade and prevents it from loosening or falling out, even if the blade and/or blade holding cavity have a degree of tolerance in one or more of their dimensions. The exemplary disclosed method and apparatus is directed to overcoming one or more of the shortcomings set forth above and/or other deficiencies in existing technology.

SUMMARY OF THE INVENTION

In one aspect, the present invention is directed to a cutting device. The cutting device includes a body member having a cavity that extends from an opening at a front end portion of the body member toward a back end portion of the body member. The cutting member also includes a cutting member partially disposed in a first portion of the cavity, and an insert member disposed in a second portion of the cavity. The cavity narrows in a direction extending from the front end portion toward the back end portion. A width of the first portion of the cavity is greater than a width of the second portion of the cavity.

In another aspect, the present invention is directed to a cutting device. The cutting device includes a body member having a cavity that extends from an opening at a front end portion of the body member toward a back end portion of the body member. The cutting device also includes a cutting member partially disposed in a first portion of the cavity, and an insert member disposed in a second portion of the cavity. The cavity narrows in a direction extending from the front end portion toward the back end portion. The insert member is tapered in the direction extending from the front end portion toward the back end portion.

DETAILED DESCRIPTION AND INDUSTRIAL APPLICABILITY

Figure 1:
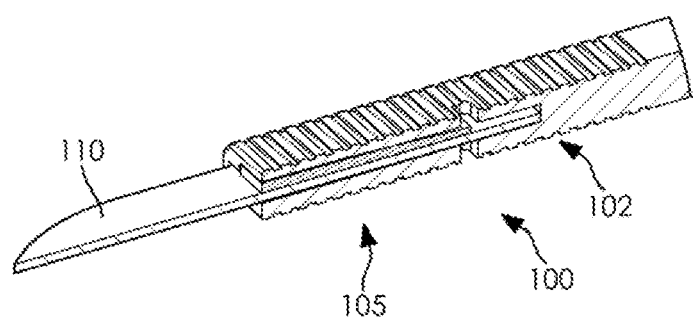
FIG. 1 is a sectional view of a long side the cutting device in accordance with an embodiment of the present invention, showing the holding cavity for the blade.

The present invention generally relates to disposable cutting devices. For example, at least some exemplary embodiments of the present invention relate to disposable scalpels (e.g., or any other suitable cutting device) having a blade holding cavity that comprises a side chamber with an insert (e.g., a plastic sheet insert) that together with the walls of the cavity secures the blade.

FIGS. 1-5 for example illustrate a cutting device 100. Cutting device 100 may for example be a scalpel (e.g., or any other suitable cutting device). In the following description of embodiments of the invention, in general, the two opposite surfaces gripped between the fingers of a hand holding cutting device 100 are referred to as its top and bottom (e.g. as the scalpel would appear if lying flat on a table). Cutting device 100 may have a body 102 having two distal end portions, a front end portion 105 that holds a blade 110, and a back end portion 115 on the opposite side of cutting device 100 from front end portion 105. Cutting device 100 may also have two opposite sides (left and right). In at least some exemplary embodiments, cutting device 100 may be of general symmetrical build, or may be configured with an ergonomical shape or surface structure, to better fit into the grip of a user's hand. Cutting device 100 may have a cover (e.g., a safety cap) 104 that may be removably attachable to front end portion 105 and/or back end portion 115.

According to at least some exemplary embodiments of the present invention, the exemplary cutting device described herein may comprise body 102 configured with a cavity 120, blade 110, and an insert 125. Cavity 120 may be open at front end portion 105, and may extend towards back end portion 115 of cutting device 100 for a distance (e.g., for a length) sufficient to accommodate the length of an internal portion of blade 110 that does not protrude from body 102. For example, the length of the internal portion of blade 110 may be at least the same length as the length of the protruding external part of blade 110. For a more secure fit for example, the internal part (e.g., the portion retained in cavity 120) of blade 110 may be 1.5, 2, 2.5, 3 or more times the length of the external part of blade 110. As disclosed further for example below, cavity 120 may include a side chamber 122.

According to at least some exemplary embodiments of the present invention and as illustrated in FIG. 1, cavity 120 may be configured to hold blade 110 and insert 125, with blade 110 protruding out of front end portion 105 of cutting device 100. Insert 125 may not protrude (or may not protrude to a significant extent) from front end portion 105. The length of cavity 120 (from a top end of front end portion 105 of body 102 toward back end portion 115) may be at least the same as the length of the internal part of blade 110, and may also for example be longer (for example to accommodate an optional weight at or near back end portion 115 to improve balance). For example, the length of cavity 120 may be about the length of the internal part (e.g., portion retained in cavity 120) of blade 110, and the length of the external part of blade 110 may correspond to the internal part as described for example herein. For example, the total length of body 102 from front to back end may be from about 1 to about 10 times the length of the cavity, or more, for example, about 2-8 times or 4-6 times the length, e.g. about 5 times the length of the cavity.

According to at least some exemplary embodiments of the present invention, a top and bottom of cavity 120 may be slightly tapered. For example, top and bottom walls of cavity 120 each may have a draft angle of about 0.5°-3.5°, 0.5°-2.5°, or about 1°-2°, with cavity 120 becoming increasingly narrower in a direction moving toward back end portion 115. A small taper/draft angle in the bottom wall of cavity 120, the top wall of cavity 120 (e.g., a side chamber top wall or "ceiling"), and/or insert 125 is for example illustrated in FIG. 3. This exemplary taper may help to accommodate tolerance in the dimensions of blade 110 (e.g. width and/or height). Additionally or alternatively, the side walls of cavity 120 and/or side walls of side chamber 122 may also include a taper/draft angle. The taper of the side walls may be substantially the same or different as the one for the top/bottom walls, and the draft angle amount (e.g., degrees) may for example similar to those described above for the top/bottom walls.

According to at least some exemplary embodiments of the present invention, side chamber 122 may be configured as a part of cavity 120 to hold insert 125, as illustrated for example in FIGS. 1-4. Side chamber 122 may for example have a smaller width than the width of cavity 120 that holds blade 110, for example to improve ease of assembly and/or to better secure blade 110. Alternatively for example, the width of cavity 120 that holds blade 110 and the width of side chamber 122 may be substantially the same. As illustrated for example in FIG. 3, side chamber 122 may be tapered to the same or to a different degree of a draft angle of cavity 120. For example, the draft angle degree may be similar to those described above for the top and/or bottom walls (e.g., of cavity 120).

According to at least some exemplary embodiments of the present invention, body 102 of cutting device 100 may be configured to receive cover (e.g., cap) 104 at one or more of its ends (e.g., at front end portion 105 and/or back end portion 115). At front end portion 105, cover 104 may be configured to fit over blade 110 when not in use and may thus prevent unintended cuts and injuries. Cover 104 may be configured to also fit on back end portion 115 for storage during use of cutting device 100, in which case back end portion 115 may be configured accordingly to fit cover 104. Cover 104 may be rotated 180° by a user and then slid over back end portion 115 for reversible attachment. Alternatively for example, e.g. when cutting device 100 is a craft knife scalpel having a circular cylindrical body, back end portion 115 may be configured with an aperture to fit cover 104 with the distal ends of cover 104 extending out to both sides of body 102 (e.g., protrusions extending from both sides), thereby prevent rolling of cutting device 100 when placed on a flat surface.

According to at least some exemplary embodiments of the present invention, body 102 may be cylindrical. For example, body 102 may be flat rectangular cylindrical in shape, e.g., when cutting device 100 is a scalpel (e.g., a surgical scalpel). For example, body 102 may have two opposing pairs of elongated (e.g., relatively longer) surfaces that are substantially parallel to each other, for example, with sides extending only a few millimeters, e.g. 1-3 mm. For example, the top and bottom of body 102 may be about 5-15 mm wide. Alternatively, body 102 may be circular cylindrical, elliptic cylindrical, octagonal cylindrical or rectangular cylindrical (e.g. including a prism). Body 102 may be hollow or solid, and if hollow it may comprise a weight, which may optionally be located in cavity 120 that may accommodate blade 110 (e.g., or the weight may be accommodated in a separate second cavity located at, near, or towards back end portion 115 of body 102).

According to at least some exemplary embodiments of the present invention, insert 125 made be made of thin plastic, for example, about 0.1-2 mm thick, e.g. 0.1-0.3, 0.3-0.6, 0.6-0.9, 0.9-1.2, 1.2-1.5, 1.5-2 mm, or more. Any plastic, thermoplastic, polymer, epoxy or resin that may for example be formed into a thin sheet may be used.

According to at least some exemplary embodiments of the present invention, body 102 and/or cover 104 may be made of one or more materials, including plastics, thermoplastics, polymers, metals, and wood.

According to at least some exemplary embodiments of the invention, body 102, a part of body 102, and/or insert 125 may be formed from a suitable thermoplastic material, which may include, for example, Acrylanitrile Butadiene Styrene (ABS), Polycarbonate (PC), Mix of ABS and PC, Acetal (POM), Acetate, Acrylic (PMMA), Liquid Crystal Polymer (LCP), Mylar, Polyamid-Nylon, Polyamid-Nylon 6, Polyamid-Nylon 11, Polybutylene Terephthalate (PBT), Polycarbonate (PC), Polyetherimide (PEI), Polyethylene (PE), Low Density PE (LDPE), High Density PE (HDPE), Ultra High Molecular Weight PE (UHMW PE), Polyethylene Terephthalate (PET), PolPolypropylene (PP), Polyphthalamide (PPA), Polyphenylenesulfide (PPS), Polystyrene (PS), High Impact Polystyrene (HIPS), Polysulfone (PSU), Polyurethane (PU), Polyvinyl Chloride (PVC), Chlorinated Polyvinyl chloride (CPVC), Polyvinylidenefluoride (PVDF), Styrene Acrylonitrile (SAN), Teflon TFE, Thermoplastic Elastomer (TPE), Thermoplastic Polyurethane (TPU), Engineered Thermoplastic Polyurethane (ETPU), or any combination thereof.

According to at least some exemplary embodiments of the present invention, body 102 may be made from one piece or from multiple pieces. For example, body 102 may be configured from two pieces, e.g. two halves, which may be substantially symmetrical or non-symmetrical with regard to their outer and/or inner shape, and their outer and/or inner surface profile.

According to at least some exemplary embodiments, body 102 may have two halves, and the part of cavity 120 that holds insert 125 may be configured as side chamber 122 with different dimensions in size compared to cavity 120, with the inner shape and surface profile of the two body halves being non-symmetrical. The outer shape and surface profile of body 102 may be symmetrical or non-symmetrical.

According to at least some exemplary embodiments, cutting device 100 may be assembled depending on the construction of body 102 as described for example above. For example, an interference fit (also known as a press fit or a friction fit) may be used. This may include an interference fit by force or temperature (thermal expansion or contraction). Adhesives may for example be used. Also for example, no adhesives may be used.

In at least some exemplary embodiments, body 102 may be a one-part piece, and blade 110 and/or insert 125 may be press fit into cavity 120 and side chamber 122, respectively, placing (e.g., press-fitting) blade 110 and insert 125 either consecutively or at the same time. Alternatively, instead of force, thermal contraction or expansion may be used, e.g. by cooling before fitting to contract the parts, joining the contracted parts, then completing the fit by allowing the parts to reach room temperature, upon which the parts expand, interfere, and are joined securely. For example, insert 125 may be shrunk by cooling to allow it to be easily placed into side chamber 122 during assembly. Adhesive may for example be used. Also for example, assembly may be achieved without use of adhesives.

In another exemplary embodiment, body 102 may be a multiple-part piece, for example, a two-part piece. For example, body 102 may be comprised of two body halves. A multiple-part body may be assembled as described herein above for a one-part body, or alternatively by joining the multiple pieces, joining the two pieces, or joining the two halves. For example, one body half may be configured with the part of cavity 120 that may hold blade 110, and the other half may be configured with side chamber 122 that may hold insert 125. Then the remaining parts (including blade 110 and insert 125) may be inserted into their respective halves of body 102, and the two halves may be joined to form cutting device 100. To join the multiple pieces, two pieces, or two halves, depending on the materials of the parts involved, mechanical fasteners, ultrasonic welding, coatings, adhesive, or any combination thereof may be used.

According to at least some exemplary embodiments of the invention, a fastening element such as a hinge or latch or similar may be disposed in or on (e.g., configured in) the parts to be joined. In this case, relatively stronger plastics may be used so that the parts remain intact during the strain of assembly. Alternatively or additionally, mechanical fasteners such as screws, rivets, pins, nuts, push on lock nuts, or clips may be used. The mechanical fasteners may be molded in place, forced, glued or expanded into holes, inserted ultrasonically or inserted with heated probes. Mechanical fasteners may be used with suitable plastic materials resilient enough to withstand the strain of fastener insertion and the stress around the fastener, depending on shape and thickness of the parts. For example, if body 102 is flat and the body parts/halves to be joined are thin, a push on lock nut or clip may be used. Also for example, screws may be used as fasteners.

In another embodiment, the material of the body parts to be joined may be plastics, which may be joined by ultrasonic welding, e.g. transmittal of sonic pulses to the parts by a resonant vibrating tool called a horn, which causes two plastic materials to vibrate against each other. The exemplary vibration both heats and fuses the parts together, without use glues or solvents. Plastic parts including those composed of blends or alloys of different resin families may be welded if their melting temperatures are within e.g. about 30° F. and their composition is compatible.

In another embodiment, the material of the body parts to be joined may be thermoplastics that are softened by coating them with a solvent, then clamping or otherwise pressing the parts together to bond them upon evaporation of the solvent. For example, elevated temperature may be used to cure the bond, and if the material of the body parts to be joined are clear materials, they may be instantly cured using high-intensity ultraviolet light.

In another exemplary embodiment, adhesive may be used exclusively to join body pieces and leaf spring, or adhesive may be used in addition to any of the joining methods described herein-above, or may be used in addition to a combination of the above-described methods.

In another exemplary embodiment, the assembly of a multiple-part body may be achieved without adhesives, without solvents, or without adhesives and without solvents.

According to at least some exemplary embodiments of the present invention, body 102 may be a one part piece, and to assemble cutting device 100 from its component parts (body, blade and insert), first blade 110 may be placed in the bottom of cavity 120 of body 102, and then insert 125 may be press fit into side chamber 122 of cavity 120. Alternatively, in another embodiment of the invention, insert 125 may be placed first, then blade 110 inserted. Optionally, for example, adhesive may be used. In an exemplary embodiment, assembly of body 102, blade 110 and insert 125 may be achieved without use of adhesives or solvents.

According to at least some exemplary embodiments of the present invention, cover 104 may be of a shape to closely fit the contours of body 102, and may be tapered slightly. For example, the inner circumference of cover 104 may match or may be slightly larger than the outer circumference of body 102 to provide a somewhat loose friction fit that is tight enough to stay on cutting device 100, but loose enough to be pulled off of easily by hand. Cover 104 may match the body's geometrical shape, e.g. a flat cylindrical body may have a flat cylindrical cap, and a circular cylindrical body may have a circular cylindrical cap.

According to at least some exemplary embodiments of the present invention, blade 110 used with the exemplary cutting device of the present invention may be constructed from a ceramic material that is capable of withstanding extended use without becoming dull or unusable. Ceramic materials appropriate for such construction include, but are not limited to, Zirconium Oxide. One of ordinary skill in the art would appreciate that there are numerous ceramic materials that could be utilized with embodiments of the present invention. Alternatively, embodiments of the present invention may be used with standard scalpel blades, for example, a metal or steel blade. According to at least some exemplary embodiments of the present invention, the blade used in the scalpel may be configured with a rounded tip to reduce the chance of injury.

According to at least some exemplary embodiments of the present invention, cavity 120 may be formed depending on the method of manufacture, e.g. by additive or reductive manufacturing/machining or by configuring a mold accordingly, e.g. with a "negative" of the cavity (e.g. a protrusion), before injection molding. Body 102 may be formed with cavity 120 during manufacturing (e.g. by a suitable mold), or may be manufactured without cavity 120, and cavity 120 may then be provided after manufacture of body 102 by taking away some of the body material with tools suitable for the material of body 102 (e.g. for cutting, broaching, milling, carving, sawing, grinding, boring, or drilling).

According to at least some exemplary embodiments of the present invention, cutting device 100 may be configured to retain a weight within a hollow cavity of body 102. When the weight is placed inside body 102 of cutting device 100, the weight may be secured in such a manner as to hold the weight in place, for example, via a compression fit within an inner wall of body 102, and/or by use of adhesive. According to at least some exemplary embodiments of the present invention, the weight may be placed towards back end portion 115 of cutting device 100 (the opposite end as blade 110), to add balance to cutting device 100, to help a user to better control the bladed end, and/or to improve the safety of using cutting device 100.

Any suitable methods and corresponding materials to form body 102 and/or cover 104 may be used. According to at least some exemplary embodiments of the present invention, cutting device 100 may be formed by 3D printing (also known as "additive" manufacturing), CNC machined parts (also known as "subtractive" manufacturing), and injection molding, as will be apparent to a person of ordinary skill in the art. Thermoplastic and thermosetting polymers, resins and elastomers, as described herein-above may be used. Many plastics, polymers and resins are known and available and can be selected and mixed depending on desired strength and flexibility, as will be apparent to a person of ordinary skill in the art.

Turning to FIG. 1, a sectional view of a long side of cutting device 100 that may be a scalpel is illustrated. In this illustration, an exemplary embodiment of the present invention is illustrated with its holding cavity 120 for blade 110.

Figure 2:
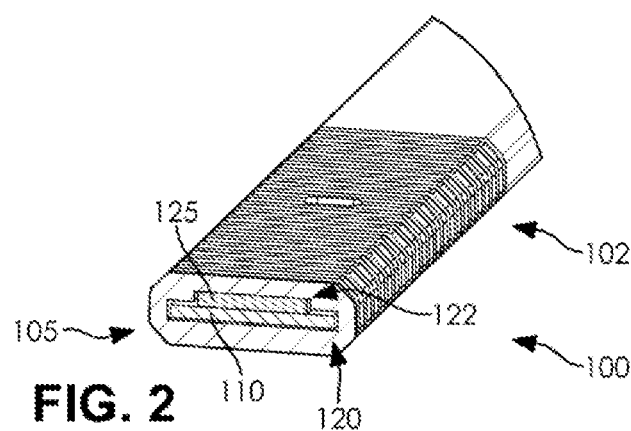
FIG. 2 is a sectional view of the front/short blade-holding side of the cutting device in accordance with an embodiment of the present invention, showing the holding cavity for the blade.

Turning to FIG. 2, a sectional view of the short blade-holding side of cutting device 100 that may be a scalpel is illustrated. In this illustration, an exemplary embodiment of the present invention is shown with the holding cavity 120 for blade 100.

Figure 3:
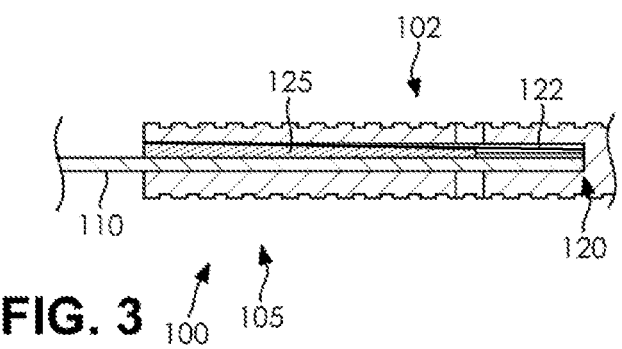
FIG. 3 is a schematic view of a cutting device in accordance with an embodiment of the present invention, showing a cross-section of the scalpel that corresponds to the surface of the cut shown in FIG. 1.

Turning to FIG. 3, a schematic view of cutting device 100 that may be a scalpel is illustrated. In this illustration, an exemplary embodiment of cutting device 100 that may be a scalpel is shown with its cross-section that corresponds to a surface of the cut illustrated in FIG. 1.

Figure 4:
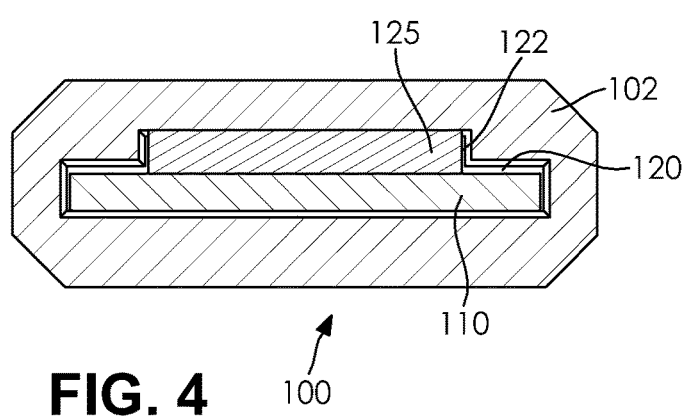
FIG. 4 is a schematic view of a cutting device in accordance with an embodiment of the present invention, showing a cross-section of the cutting device that corresponds to the surface of the cut shown in FIG. 2.

Turning to FIG. 4, a schematic view of cutting device 100 that may be a scalpel is illustrated. In this illustration, an exemplary embodiment of cutting device 100 that may be a scalpel is shown with its cross-section that corresponds to a surface of the cut illustrated in FIG. 2.

Figure 5:
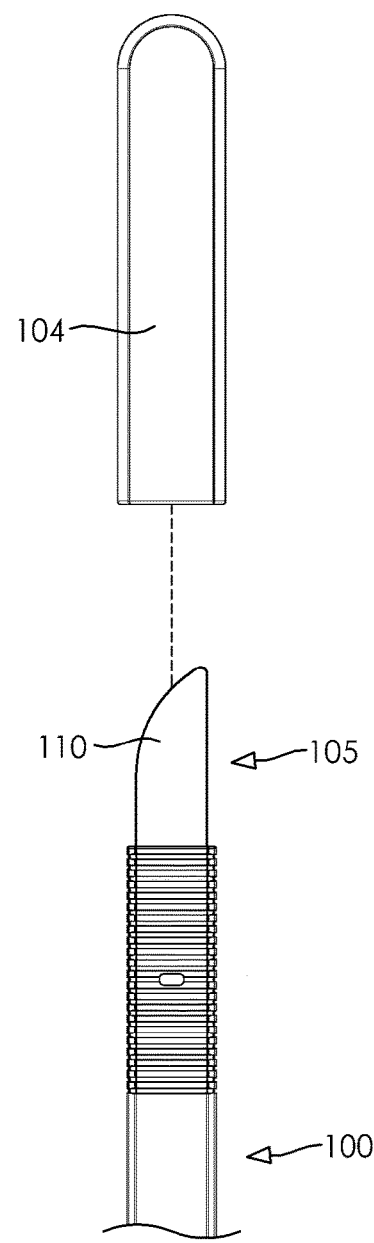
FIG. 5 is an orthogonal view of the cutting device in accordance with embodiments of the present invention, showing its top/bottom.

Turning to FIG. 5, an orthogonal view of cutting device 100 that may be a scalpel is illustrated. In this illustration, a top and bottom are shown.

According to at least some exemplary embodiments of the present invention, a cutting device (e.g., cutting device 100) may include a body member (e.g., body 102) having a cavity (e.g., cavity 120) that extends from an opening at a front end portion (e.g., front end portion 105) of the body member toward a back end portion (e.g., back end portion 115) of the body member. For example, the exemplary cutting device may also include a cutting member (e.g., blade 110) partially disposed in a first portion of the cavity and an insert member (e.g., insert 125) disposed in a second portion (e.g., side chamber 122) of the cavity. The cavity may narrow in a direction extending from the front end portion toward the back end portion, and a width of the first portion of the cavity may be greater than a width of the second portion of the cavity. Also for example, the insert member may be tapered in a direction extending from the front end portion toward the back end portion. Further for example, a width of the cutting member may be greater than a width of the insert member, and a length of the cutting member may be greater than a length of the insert member. Additionally for example, an inserted length of the cutting member that is disposed in the cavity may be greater than or equal to an exposed length of the cutting member that protrudes from the cavity. Also for example, the cutting member may be formed from ceramic material (e.g., from Zirconium Oxide), and the cutting device may be a surgical scalpel. Further for example, the cavity may narrow in the direction extending from the front end portion toward the back end portion at a taper angle of between about 0.5° and about 2.5°, and a bottom wall and a top wall of the cavity may be tapered. Additionally for example, the insert member may have a thickness of between about 0.1 mm and about 2 mm. Also for example, a width of the first portion of the cavity may be greater than a width of the second portion of the cavity. Further for example, a weight may be disposed at the rear end portion. Additionally for example, a cover may be removably attachable to the front end portion and the back end portion. Also for example, the cutting device may be a scalpel. Further for example, the insert member may be a plastic sheet member.

According to at least some exemplary embodiments of the present invention, the exemplary cutting device may be a scalpel including a scalpel body member (e.g., body 102) having a cavity (e.g., cavity 120) that extends from an opening at a front end portion (e.g., front end portion 105) of the scalpel body member toward a back end portion (e.g., back end portion 115) of the scalpel body member. For example, the scalpel may also include a scalpel blade (e.g., blade 110) partially disposed in a first portion of the cavity and a plastic sheet member (e.g., insert 125) disposed in a second portion (e.g., side chamber 122) of the cavity. Also for example, the cavity may narrow in a direction extending from the front end portion toward the back end portion, and a width of the first portion of the cavity may be greater than a width of the second portion of the cavity. Further for example, a total length of the scalpel body member may be between about 4 times and about 6 times of a length of the cavity.

The exemplary disclosed apparatus and method may be used in any suitable application for utilizing a cutting device. For example, the exemplary disclosed apparatus and method may be used in any suitable technique for providing and/or using a disposable cutting device. For example, the exemplary disclosed apparatus and method may be used in any suitable application for providing and using a disposable scalpel.

The exemplary disclosed apparatus and method may provide a cutting device that may be used safely and efficiently. For example, the exemplary disclosed apparatus and method may effectively secure a blade to a cutting device and prevent it from loosening or falling out. For example, the exemplary disclosed apparatus and method may effectively secure a blade to a cutting device even if the blade and/or blade holding cavity have a degree of tolerance in one or more of their dimensions. Further for example, the exemplary disclosed apparatus and method may provide an effective technique for providing a disposable cutting device such as, e.g., a disposable scalpel.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature rather than restrictive.

What is claimed is:

1. A cutting device, comprising:
   a body member having a cavity that extends from an opening at a front end portion of the body member toward a back end portion of the body member;
   a cutting member partially disposed in a first portion of the cavity; and
   an insert member disposed in a second portion of the cavity;
   wherein the cavity narrows in a direction extending from the front end portion toward the back end portion;
   wherein a width of the first portion of the cavity is greater than a width of the second portion of the cavity; and
   wherein the cavity is completely surrounded by wall portions of the body member.

2. The cutting device of claim 1, wherein the insert member is tapered.

3. The cutting device of claim 1, wherein the insert member is tapered in the direction extending from the front end portion toward the back end portion.

4. The cutting device of claim 1, wherein a width of the cutting member is greater than a width of the insert member.

5. The cutting device of claim 1, wherein a length of the cutting member is greater than a length of the insert member.

6. The cutting device of claim 1, wherein an inserted length of the cutting member that is disposed in the cavity is greater than or equal to an exposed length of the cutting member that protrudes from the cavity.

7. The cutting device of claim 1, wherein the cutting member is formed from ceramic material.

8. The cutting device of claim 1, wherein the cutting device is a disposable surgical scalpel.

9. The cutting device of claim 1, wherein the cavity narrows in the direction extending from the front end portion toward the back end portion at a taper angle of between about 0.5° and about 2.5°.

10. The cutting device of claim 9, wherein a top wall of the wall portions of the body member is tapered.

11. The cutting device of claim 1, wherein the insert member has a thickness of between about 0.1 mm and about 2 mm.

12. A cutting device, comprising:
    a body member having a cavity that extends from an opening at a front end portion of the body member toward a back end portion of the body member;
    a cutting member partially disposed in a first portion of the cavity; and
    an insert member disposed in a second portion of the cavity;
    wherein the cavity narrows in a direction extending from the front end portion toward the back end portion;
    wherein the insert member is tapered in the direction extending from the front end portion toward the back end portion; and
    wherein the insert member is disposed between the cutting member on a first side and a wall of the body member on a second side that is opposite to the first side.

13. The cutting device of claim 12, wherein a width of the first portion of the cavity is greater than a width of the second portion of the cavity.

14. The cutting device of claim 12, wherein the cutting member is formed from Zirconium Oxide.

15. The cutting device of claim 12, further comprising a cover that is removably attachable to the front end portion and the back end portion.

16. The cutting device of claim 12, wherein the cutting device is a disposable scalpel.

17. The cutting device of claim 12, wherein the insert member is a plastic sheet member.

18. A scalpel, comprising:
    a scalpel body member having a cavity that extends from an opening at a front end portion of the scalpel body member toward a back end portion of the scalpel body member;
    a scalpel blade partially disposed in a first portion of the cavity; and
    a plastic sheet member disposed in a second portion of the cavity;
    wherein the cavity narrows in a direction extending from the front end portion toward the back end portion;
    wherein a width of the first portion of the cavity is greater than a width of the second portion of the cavity; and
    wherein the cavity is completely surrounded by wall portions of the scalpel body member.

19. The scalpel of claim 18, wherein a total length of the scalpel body member is between about 4 times and about 6 times of a length of the cavity.

* * * * *